United States Patent [19]
Burke et al.

[11] Patent Number: 5,601,563
[45] Date of Patent: Feb. 11, 1997

[54] ORTHOPAEDIC MILLING TEMPLATE WITH ATTACHABLE CUTTING GUIDE

[75] Inventors: Dennis W. Burke, 245 Highland St., Milton, Mass. 02186; Terry L. Dietz, Columbia City, Ind.; Daniel O'Connor, East Taunton, Mass.

[73] Assignees: Zimmer, Inc., Warsaw, Ind.; Dennis W. Burke, Milton, Mass.

[21] Appl. No.: 519,496

[22] Filed: Aug. 25, 1995

[51] Int. Cl.⁶ ........................................................ A61F 5/00
[52] U.S. Cl. ............................. 606/86; 606/79; 606/62
[58] Field of Search ............................. 606/79, 62, 88, 606/89, 86, 87, 96, 53, 102

[56] References Cited

U.S. PATENT DOCUMENTS

| 4,457,307 | 7/1984 | Stillwell | 128/317 |
|---|---|---|---|
| 4,459,985 | 7/1984 | McKay et al. | 128/303 R |
| 4,467,801 | 8/1984 | Whiteside | 128/303 R |
| 4,487,203 | 12/1984 | Androphy | 128/303 R |
| 4,567,885 | 2/1986 | Androphy | 128/92 H |
| 4,574,794 | 3/1986 | Cooke et al. | 128/92 H |
| 4,703,751 | 11/1987 | Pohl | 606/87 |
| 4,721,104 | 1/1988 | Kaufman et al. | 128/92 VW |
| 4,722,330 | 2/1988 | Russell et al. | 128/92 |
| 4,759,350 | 7/1988 | Dunn et al. | 128/92 |
| 4,787,383 | 11/1988 | Kenna | 128/303 R |
| 4,892,093 | 1/1990 | Zarnowski et al. | 606/82 |
| 4,926,847 | 5/1990 | Luckman | 606/88 |
| 4,952,213 | 8/1990 | Bowman et al. | 606/79 |
| 5,035,699 | 7/1991 | Coates | 606/86 |
| 5,047,032 | 9/1991 | Jellicoe | 606/83 |
| 5,053,037 | 10/1991 | Lackey | 606/79 |
| 5,092,869 | 3/1992 | Waldron | 606/82 |
| 5,098,436 | 3/1992 | Ferrante et al. | 606/88 |
| 5,112,336 | 5/1992 | Krevolin et al. | 606/96 |
| 5,122,144 | 6/1992 | Bert et al. | 606/88 |
| 5,129,907 | 7/1992 | Heldreth et al. | 606/80 |
| 5,129,908 | 7/1992 | Petersen | 606/80 |
| 5,171,244 | 12/1992 | Caspari et al. | 606/88 |
| 5,171,276 | 12/1992 | Caspari et al. | 623/16 |
| 5,176,684 | 1/1993 | Ferrante et al. | 606/86 |
| 5,180,384 | 1/1993 | Mikhail | 606/80 |
| 5,190,547 | 3/1993 | Barber et al. | 606/79 |
| 5,201,768 | 4/1993 | Caspari et al. | 623/20 |
| 5,207,680 | 5/1993 | Dietz et al. | 606/86 |
| 5,207,711 | 5/1993 | Caspari et al. | 623/20 |
| 5,228,459 | 7/1993 | Caspari et al. | 128/898 |
| 5,234,433 | 8/1993 | Bert et al. | 606/88 |
| 5,263,498 | 11/1993 | Caspari et al. | 128/898 |
| 5,304,181 | 4/1994 | Caspari et al. | 606/80 |
| 5,344,423 | 9/1994 | Dietz | 606/87 |
| 5,417,695 | 5/1995 | Axelson, Jr. | 606/89 |
| 5,454,816 | 10/1995 | Ashby | 606/88 |
| 5,474,559 | 12/1995 | Bertin et al. | 606/89 |

FOREIGN PATENT DOCUMENTS

| 0104732 | 4/1984 | European Pat. Off. | A61B 17/14 |
|---|---|---|---|
| 555003 | 8/1993 | European Pat. Off. | 606/88 |

Primary Examiner—Michael Powell Buiz
Assistant Examiner—Kevin Truong
Attorney, Agent, or Firm—Todd A. Dawson

[57] ABSTRACT

The invention is directed to milling instrumentation used for preparing a bone for receiving a prosthetic implant. The milling instrumentation includes a milling template for connection to an exposed end of a bone for guiding a milling device along the bone. A detachable cutting guide is removably connected to the milling template to permit a surgeon to either utilize either milling or cutting techniques in resecting the bone.

12 Claims, 3 Drawing Sheets

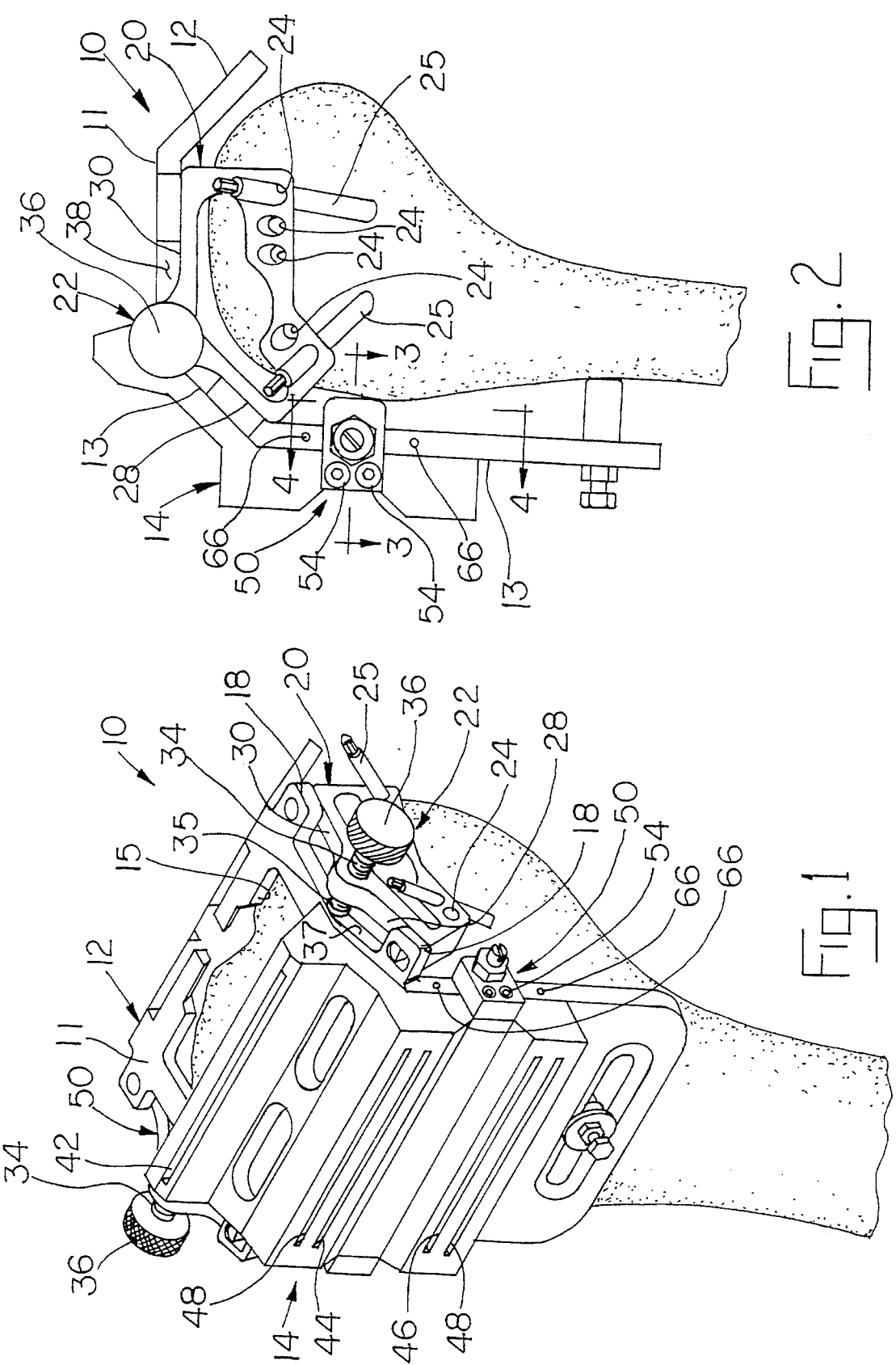

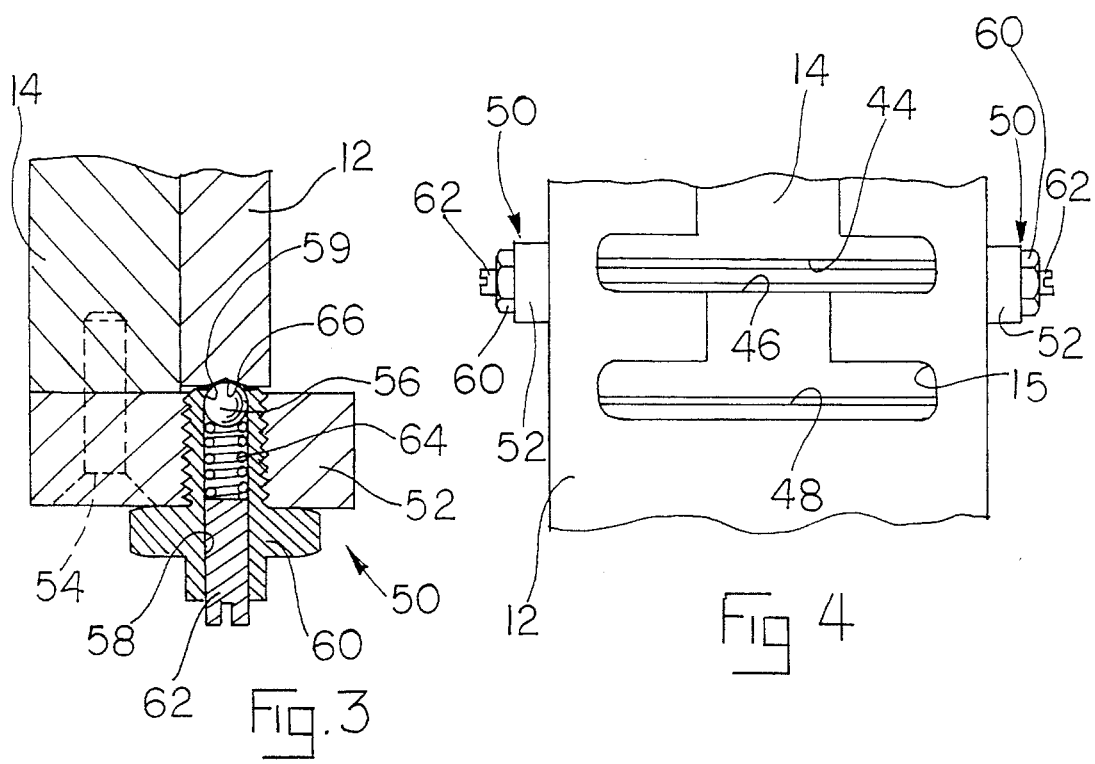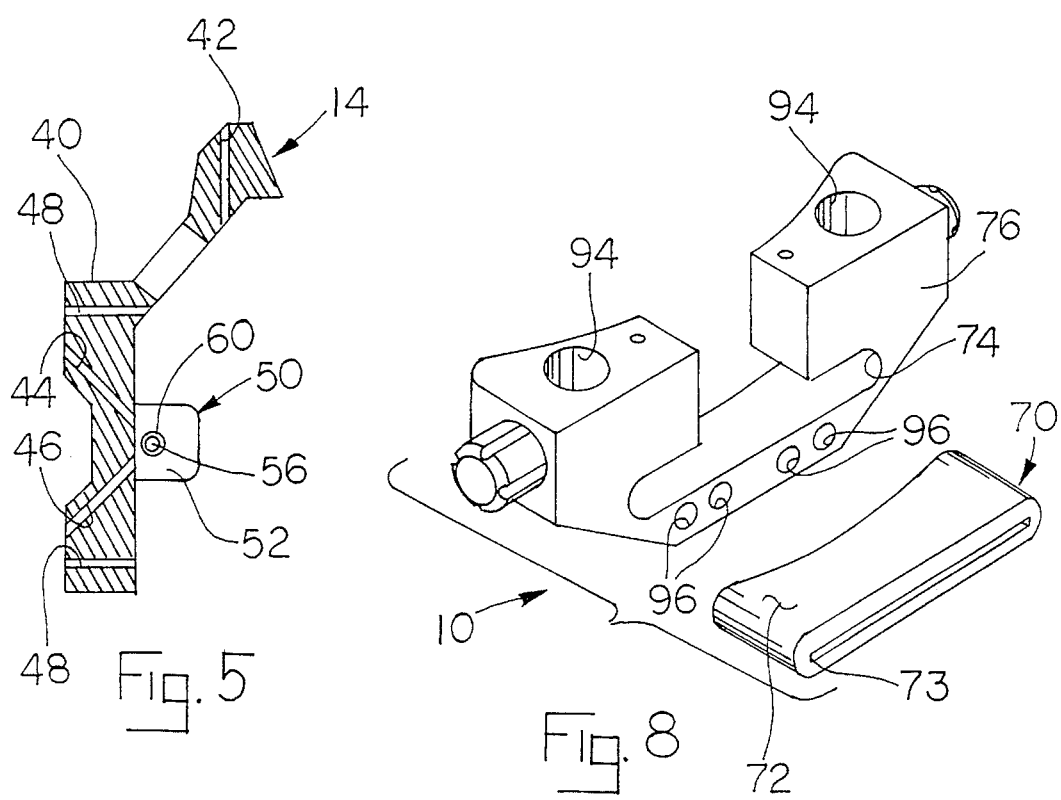

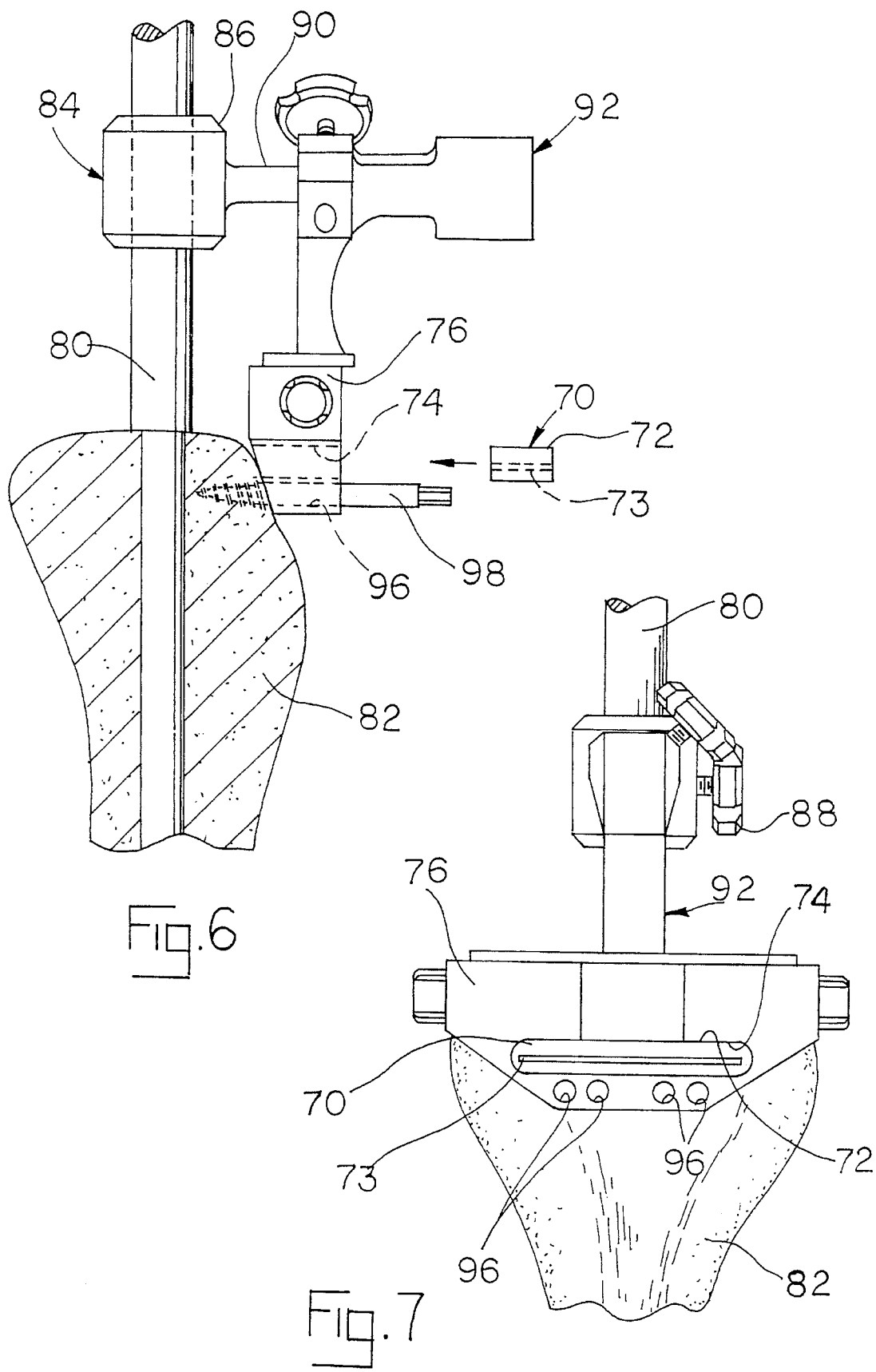

5,601,563

ORTHOPAEDIC MILLING TEMPLATE WITH ATTACHABLE CUTTING GUIDE

FIELD OF THE INVENTION

The present invention relates to instrumentation used in orthopaedic surgery, and, more particularly, relates to instrumentation used to prepare bone for receiving a prosthesis.

BACKGROUND OF THE INVENTION

In an orthopaedic surgery to replace part or all of a patient's joint with a prosthetic implant, a portion of the implant receiving bone is prepared to closely match the mating surfaces of the implant. During an orthopaedic surgery to replace a knee joint, the distal end of the femur is prepared to accommodate a femoral knee component and the proximal end of the tibia is prepared to accommodate a tibial component.

In the preparation of the femur, for example, one or more milling templates are placed adjacent the distal femur in a specific order to resect portions of the femur in succession. These milling templates are generally individually aligned by the surgeon with reference to specific anatomic landmarks and a guide platform connected to an intramedullary rod. At times and in particular situations, the surgeon may wish to either utilize either a milling device or a cutting device to resect the bone. Presently, the surgeon has a choice of which device or technique to utilize, but for each of technique, a separate milling template or cutting guide has to be individually fixated and oriented to the bone.

What is needed in the art is a system allowing a cutting guide to be used in conjunction with a milling template without removing the milling template.

SUMMARY OF THE INVENTION

The milling instrumentation of the invention improves on the prior art systems by providing a milling guide connected to a bone, such as a femur, to which a surgeon may attach a cutting guide. The cutting guide may be utilized without removing the milling guide from the bone. A powered cutting device, having a blade connected thereto, is guided by the slots within the cutting guide, the blade passing through the milling guide and into contact with a portion of the bone.

An advantage of the milling template system of the present invention is that it provides a novel milling and cutting instrument for preparing a bone surface to accommodate an orthopaedic implant. Exactly the same fixation steps are utilized whether the surgeon is milling or cutting a bone.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a perspective view of one embodiment according to the present invention which is connectable to a bone to guide a cutting device;

FIG. 2 is an elevational side view of the embodiment of FIG. 1;

FIG. 3 is a cross sectional view of the embodiment of FIG. 2, taken along the line 3—3 and viewed in the direction of the arrows;

FIGS. 4 is a fragmentary rear view of the embodiment of FIG. 2, taken along the line 4—4 and viewed in the direction of the arrows;

FIG. 5 is a cross sectional side view of the cutting guide of the embodiment of FIG. 2;

FIG. 6 is an elevational side view of another embodiment of the invention disposed on top of a bone;

FIG. 7 is a front elevational view of the embodiment of FIG. 6;

FIG. 8 is an exploded perspective view of a portion of the embodiment shown in FIG. 6.

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION OF THE INVENTION

Referring now to FIGS. 1 and 2, there is shown a perspective and side view of a milling instrumentation system 10 of the present invention. System 10 includes a milling template 12 to which is attachable a separate cutting guide 14. Both milling template 12 and cutting guide 14 are formed of metal, preferably stainless steel or another medical grade metal, although other materials may be utilized.

Milling template 12 is generally C-shaped including a base member 11 and a plurality of walls 13 defining a set of reference planes. Depending on the particular size and shape of the prosthesis to be attached to the bone, different numbers of milled planes on the bone may be required, thereby requiring different numbers of walls or reference planes on milling template 12. A milling cutter (not shown) may be guided relative to the bone using milling template 12. Particularly, a milling cutter may be guided through openings 15 through milling template 12 to thereby resect bone. For details of such milling instrumentation, reference is made to co-pending U.S. patent application Ser. No. 08/169,459 U.S. Pat. No. 5,474,559, May 22, 1996 which is assigned to the assignee of the present invention and expressly incorporated herein by reference.

Milling template 12 is generally attached to bone by either attaching to a base by extending tabs 18, or directly attaching to the bone by means of pins, or screws. One type of base for attaching milling template 12 to a bone is a femoral base 20 as illustrated in FIGS. 1 and 2. Other types of bases to which milling template 12 can be attached are possible, as would be obvious to one skilled in the art.

In practice, two femoral bases 20 are required; however, only one need be described here as the two bases in use are simply mirror images of one another. Femoral base 20 includes a body 26 defining a substantially flat anterior distal surface 28 and a substantially flat posterior distal surface 30. The body 26 is curved slightly such that the surfaces 28 and 30 are not in the same plane. A locking mechanism 22 is situated between surfaces 28 and 30 and includes a bore extending transversely through the body 26. Locking mechanism 22 may be constructed with a screw 34 threadably accommodated by base 20 and including at one end, a smooth conical tip 35, and at the other end, a knob 36. The milling template 12 includes an opening 37 which includes an inclined wall 38. In use, to lock milling template 12 to base 20, screw 34 is rotated until its conical tip 35 contacts inclined wall 38 to clamp milling template 12 between tip 35, base 20 and the bone.

As illustrated in the drawings, femoral base 20 includes a plurality of openings 24. Two openings 24 are positioned anteriorly and three are positioned posteriorly on the body 26. As illustrated best in FIG. 2, the anterior openings 24 are angled such that a screw 25 passing therethrough is directed proximally and posteriorly within the bone. The posterior openings 24 are angled such that a screw 25 passing therethrough is directed proximally and anteriorly within the bone. Therefore, if screws 25 are inserted through at least one anterior opening and at least one posterior opening on body 26, the screws converge toward each other to thereby securely lock femoral base 20 to the bone. Preferably, the diameter of the shaft of the screw 25 passing through the body opening should closely match the diameter of openings 24 to assist in the mechanical interlock being formed.

As an alternative to current systems limited to only utilizing a milling machine such as those having a burr, the present invention includes a cutting guide 14 removably attachable to milling template 12 to give a surgeon the option of connecting a cutting guide to the milling template to resect the bone using a standard cutting device such as an oscillating or reciprocating powered surgical saw (not shown).

The five-in-one cutting guide 14 of the instrument set of the invention is illustrated in FIGS. 1 through 5 and includes a body 40 including a slight bend therein as shown. A plurality of slots are formed in body 40 for resecting different areas of the connected bone. For example, in use with a femur, a slot 42 is formed in body 40 and inclined so as to guide a saw blade along a path for resection of anterior condyles of the bone. A slot 44 is formed in body 40 inclined so as to guide a saw blade along the path for forming a chamfered surface. Use of this slot 44 may necessitate a relocation of cutting guide 14 prior to cutting. A slot 46 is formed in body 40 and inclined so as to guide a saw blade for forming another chamfered surface. Finally, a pair of aligned slots 48 are provided in base 40 for guiding a saw blade for the resection of the distal surface of the femur. It is possible to alter the angles of slots 42–48 to resect different size femurs, while the cutting guide may also be adapted for use on different bones, such as the tibia to be discussed later.

Cutting guide 14 is attachable or connectable to milling template 12 by a connection means, such as a snap fit fixture 50. Fixture 50, only one of which is shown in FIG. 3, includes a locator block 52 attached to cutting guide 14 by means of fasteners such as screws 54. A member, such as a steel ball 56, is disposed within a longitudinal bore 58 in an adjustment screw 60. Ball 56 is held in bore 58 by, on one side, a narrowed portion 59 of bore 58 such that the diameter of bore 58 at the portion point is less than the diameter of ball 56, and, on the other side, by a plug 62. Plug 62 is retained within bore 58 by any sufficient means such as an interference fit or by a threaded connection with adjustment screw 60. A biasing means, such as spring 64, is disposed within bore 58 between plug 62 and ball 56 to bias ball 56 toward the narrowed portion 59 of bore 58. The location and orientation of the narrowed portion 59 permits a portion of ball 56 to be located outside of bore 58. Other mechanisms of disposing a biased ball within bore 58 could also be utilized. Adjustment screw 60 is threadedly disposed within locator block 52 so that the location of ball 56 relative to locator block 52 may be adjusted.

The biasing of ball 56 in each snap-fit fixture 50 is utilized to form the snap-fit connection between cutting guide 14 and milling guide 12. Detents or recesses 66 are formed in the edges of milling guide 12 and serve to provide locations into which balls 56 may interfit to removably connect cutting guide 14 to milling guide 12.

To connect cutting guide 14 to milling guide 12, the surgeon locates cutting guide 14 over milling guide 12 so that a slot 42, 44, 46, or 48 will be located adjacent an opening 15 as shown in FIG. 4. The slots of cutting guide 14 need to have access to the bone, such as through template opening 15, or equivalently over or under milling guide 12, so that a cutting blade may be inserted in a slot and thereafter into contact with the bone to be resected. For these locations of cutting guide 12, recesses 66 will be placed along the edges of milling guide 14 so that as cutting guide 12 and milling guide 14 are pressed together, balls 56 will be removably caught within recesses 66, thereby connecting together cutting guide 14 and milling template 12. The bias of spring 64 provides the connection force between guide 14 and template 12. Other connection methods may also be utilized to assist in locking cutting guide 12 to milling template 14, such as set screws or the like.

An alternative embodiment, as utilized for example in resecting a tibia 82, is shown in FIGS. 6–8 in which a tibia milling template or base 76 is utilized with a cutting guide or saw guide 70. Saw guide 70 includes a slot 73 for guiding a cutting blade (not shown).

As shown in FIGS. 6 and 7, an intramedullary rod 80 is disposed within the intramedullary canal within tibia 82. A tibial boom 84 is attached to intramedullary rod 80 and includes a collar 86 with a thumbscrew 88 threadingly received therein, to lock tibial boom 84 with intramedullary rod 80 when tightened. An extending arm 90 of boom 84 extends away from collar 86 in a direction generally perpendicular to the longitudinal axis of intramedullary rod 80. A connector device 92, as shown in FIGS. 6 and 7, is connectable to extending arm 90 via a thumbscrew 94 (FIG. 6).

Base 76 may be removably connected to intramedullary rod 80 via connector device 92 and tibial boom 84. One way of creating such a connection is that base 76 may include an attachment means such as openings 94 which are sized and configured to mate with protuberances (not shown) on the bottom of connector device 92. Alternatively, other methods may be used to attach base 76 with connector 92, or they may be constructed together monolithically. In all cases, tibia base 76 will include an attachment means, such as openings 94 or other fixtures, to which a tibial milling template may attach.

Tibial milling base 76 includes a plurality of through bores 96 for attaching base 76 to tibia 82 when in an aligned position. Each bore 96 receives a fixation pin 98 (FIG. 6) which is screwed into tibia 82.

In this embodiment, as according to the invention, the connection between the tibia milling base 76 and cutting guide, a cutting block or saw guide 70 in this case, may comprise a particular outside surface 72 contoured to interfit within an opening 74 of tibia milling base 76. Such a connection would entail an interference fit to firmly connect saw guide 70 to tibia template 76.

Alternatively, other connection mechanisms between saw guide 70 and tibia template 76 may be utilized, such as the snap fit fixation device as in the femoral embodiment above, set screws, lock pins, or other detachable mechanisms to permit selective insertion, locking, and removal of saw guide 70 relative to opening 74.

The tibial milling instrumentation assembly as shown in FIGS. 6–8, permits a surgeon to attach a tibia milling template (not shown) or a tibia saw guide to allow either milling or cutting of tibia 82.

In use on a femur, the surgeon establishes the femoral bases 20 in the same manner as described in copending U.S. patent application Ser. No. 08/169,459. However, instead of connecting a femoral cutting guide 14 to the femoral bases 20, the surgeon attaches the five in one cutting guide 14 to milling template 12. With cutting guide 14 connected to milling template 14 by the biased snap fit fixture 50 (in a preferred embodiment), the surgeon inserts a blade through a slot to make the cuts necessary for placement of a prosthetic knee implant without ever moving, shifting or otherwise reorienting or changing the milling template 12. By making all the cuts necessary without changing guides or templates, the relative precision between the cuts made can be more precisely controlled, thus leading to a better fitting implant.

Operation of the second embodiment utilized with a tibia, is generally similar, with the same steps of fixating tibia milling base 74, then connecting either a tibial milling template or saw guide 70 to base 74. A cutting blade is then utilized on the tibia through saw guide slot 73. The above system gives the surgeon greater flexibility to utilize a milling or cutting resection technique of choice with a single fixation procedure.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An apparatus for guiding a cutting device to remove portions of the bone for accommodation of a prosthetic implant, said apparatus comprising:

a milling template attachable to bone, said milling template having at least one slot extending therethrough configured to accommodate a milling device;

a cutting guide for guiding a cutting blade said cutting guide having at least one slot extending therethrough configured to accommodate a cutting blade;

connection means engaging said milling template and said cutting guide for removably connecting said cutting guide to said milling template such that said slot in said cutting guide is aligned with the cutting slot in said milling template, said slot in said milling template being wider transverse to its longitudinal direction than the slot in said cutting guide.

2. The apparatus of claim 1 in which said connection means includes a snap fit fixture attached to one of said milling template and said cutting guide.

3. The apparatus of claim 2 in which said snap fit fixture includes a spring loaded member that engages the other of said milling template and said cutting guide.

4. The apparatus of claim 3 in which said other of said milling template and said cutting guide includes a recess into which said spring loaded member engages.

5. The apparatus of claim 1 in which said cutting guide includes a plurality of cutting blade openings.

6. The apparatus of claim 1 in which said milling template includes an opening, said connection means comprising an outer contoured surface that interfits and engages said milling template opening.

7. The apparatus of claim 1 in which said milling template includes an opening, said cutting guide including a slot, said slot aligned with said milling template opening to allow the cutting blade to extend through said slot and said opening to the bone.

8. The apparatus of claim 1 in which said milling template is a femoral milling template.

9. The apparatus of claim 1 in which said cutting guide is a five-in-one femoral cutting guide.

10. A method of guiding a cutting blade during an orthopaedic surgery, comprising the steps of:

fixating a milling template relative to a bone to be cut, said milling template having at least one slot extending therethrough;

providing a cutting guide having a cutting blade opening;

connecting said cutting guide to said milling template so that a cutting blade may be guided by said cutting guide wherein said cutting blade opening of said cutting guide overlies said slot in said milling template;

inserting a cutting blade through said cutting blade opening and said slot in said milling template so that the cutting blade contacts the bone.

11. The method of claim 10 in which said connecting step includes inserting said cutting guide into an opening in said milling template.

12. The method of claim 10 in which said connecting step includes snap locking said cutting guide to said milling template with a spring loaded member.

* * * * *